(12) United States Patent
Wallevik et al.

(10) Patent No.: US 7,021,123 B2
(45) Date of Patent: Apr. 4, 2006

(54) RHEOLOGICAL AND CALORIMETRIC TESTING METHOD

(75) Inventors: Olafur H. Wallevik, Reykjavik (IS); Paul Sandberg, Beverly, MA (US); David F. Myers, Acton, MA (US)

(73) Assignee: W. R. Grace & Co.-Conn., Columbia, MD (US)

( * ) Notice: Subject to any disclaimer, the term of this patent is extended or adjusted under 35 U.S.C. 154(b) by 0 days.

(21) Appl. No.: 11/054,014

(22) Filed: Feb. 9, 2005

(65) Prior Publication Data

US 2005/0138991 A1 Jun. 30, 2005

Related U.S. Application Data

(63) Continuation of application No. 10/741,747, filed on Dec. 19, 2003.

(51) Int. Cl.
- *G01N 11/14* (2006.01)
- *G01N 11/10* (2006.01)
- *G01N 11/00* (2006.01)

(52) U.S. Cl. .......... 73/54.02; 73/54.38; 73/54.39; 73/54.28

(58) Field of Classification Search .......... 73/54.01, 73/54.02, 54.38, 54.39, 54.23, 54.28, 54.03
See application file for complete search history.

(56) References Cited

U.S. PATENT DOCUMENTS

| | | | |
|---|---|---|---|
| 5,303,578 A | 4/1994 | Williams et al. | 73/54.24 |
| 5,321,974 A | 6/1994 | Hemmings et al. | 73/54.31 |
| 5,546,791 A | 8/1996 | Meeten | 73/54.28 |
| 5,610,325 A | 3/1997 | Rajagopal et al. | 73/54.39 |
| 5,631,409 A | 5/1997 | Rajagopal et al. | 73/54.35 |
| 6,227,039 B1 | 5/2001 | Te'eni | 73/54.03 |
| 2003/0154772 A1* | 8/2003 | Jackson | 73/54.28 |
| 2003/0233867 A1 | 12/2003 | Hall | 73/54.28 |
| 2005/0103119 A1* | 5/2005 | Shtakelberg et al. | 73/803 |

OTHER PUBLICATIONS

American Society for Testing and Materials, Designation: C 1074-98, "Standard Practice for Estimating Concrete Strength by the Maturity Method", Mar. 1999, pp1-8.
American Society for Testing and Materials, Designation: C 918-97, "Standard Test Method for Measuring Early-Age Compressive Strength and Projecting Later-Age Strength", Mar. 1997, pp1-6.
Engineeringtalk, "Testing the flow properties of fresh cement", http://www.engineeringtalk.com/news/mag/mag104.html, Jun. 26, 2001, printed Mar. 2004.

(Continued)

*Primary Examiner*—Hezron Williams
*Assistant Examiner*—Tamiko Bellamy
(74) *Attorney, Agent, or Firm*—Craig K. Leon; William L. Baker (57) ABSTRACT

Device and methods for rotationally mixing and rheological testing of sample liquids, such as cement particle suspensions, employ mixing blades and shear-resistant members having substantially noncoincident orbital paths. Rheology is assessed by measuring the resistance of the liquid to rotation of the device. Both rheological and calorimetric testing can be performed during mixing, which ensures uniformity of rheology and hence the accuracy of results.

23 Claims, 2 Drawing Sheets

OTHER PUBLICATIONS

Journal of Research of the National Institute of Standards and Technology, "Concrete Mixing Methods and Concrete Mixers: State of the Art", vol. 106, No. 2, Mar.-Apr. 2001, pp. 391-399.

MMIII Magna Projects & Instruments Limited, "TTPT:The Tattersall Two-Point Workability Test for Fresh Cement and Conrete and Other Materials", http://www.magna-projects.com/ttpt.htm, Jan. 2003, printed Mar. 2004.

Wallevik, "Ein Zweitageskurs in Rheology of Fresh Concete and Mortar", Eheologie Seminar, TBR Technologiezentrum GmbH & Co. KG, Nov. 2001.

Wallevik, "The BML Viscometer", Rheology of cement suspensions, 2000, pp2-2 through 2-19.

Vachon, "ASTM Puts Self-Consolidating Concrete to the Test", American Society for Testing and Materials, http://www.astm.org/SNEWS/JULY_2002/vachon_jul02.html, Jul. 2002, printed Apr. 2003.

* cited by examiner

RHEOLOGICAL AND CALORIMETRIC TESTING METHOD

CROSS-REFERENCE TO RELATED ART

This application is a continuation of U.S. patent application Ser. No. 10/741,747 filed Dec. 19, 2003, which is incorporated in its entirety by reference herein.

FIELD OF THE INVENTION

The present invention relates to a rotational mixing and rheology measuring device suitable for use with viscous fluids, and especially for particle suspensions such as cement, mortar, and concrete slurries.

BACKGROUND OF THE INVENTION

As mentioned in U.S. Pat. No. 5,546,791 of Meeten, the rheology or thixotropy of granular fluid slurries, such as cement slurries or drilling mud, can be useful for determining the behaviour of the resultant material. The current standard rheology measurement, as specified by the American Petroleum Industry (API), involves testing of samples in a cup container, and placing a rotor/stator device into the cup. The rotor/stator device comprises a cylindrical, motor-driven rotor having a vaned stator coaxially mounted on the rotation axis. Rotation of the rotor applies torque to the stator. Rate of rotation is compared to the applied torque to determine rheological characteristics of the cup-contained sample.

Meeten observed that rheometers may be inaccurate due to so-called end effects, such as "slippage at the wall" of particle-containing liquid in the container cup, and such as "particle migration" towards the bottom of the cup due to gravity. End effects arise from the torque generated by flow from the ends of the concentric cylinders that comprise the rotor/stator arrangement. Such effects can lead to significant inaccuracies in calculating shear forces applied to the sample fluid, and, hence, its rheological properties.

The first phenomenon known as "slippage at the wall" occurs when the fluid suspension is depleted of particles near the walls of the mixing container. This can, in turn, reduce significantly the measured viscosity and yield stress, consequently leading to large errors in measured values.

The second phenomenon, known as "particle migration," is primarily caused by gravity, as mentioned above, and also by centrifugation effects. The effect of gravity is to reduce the particle content in the sample zone where the yield stress is measured, and therefore the inaccuracy for rheological measurement is increased for samples mixed using high shear forces. Furthermore, the build-up of solids below the rotor/stator device may cause extra torque to be transmitted to the stator, further increasing error. Meeten further observed that centrifugation was particularly apparent in the external rotor arrangement specified by API. This centrifugation effect decreased the number of particles near the inside of the rotor, thus increasing the inaccuracy of the torque measurement and data obtained.

Meeten further observed that various attempts had been made to reduce one or more of the effects outlined above. These attempts include the provision of a pump and baffle arrangement, for example, as described in SPE Paper Production Engineering, November 1990, pp 415–424. In this publication, the authors Shah and Sutton provided slots at the upper end of the rotor and a helical flange around the outside of the rotor. These were intended to provide flow through the rheometer and to prevent build-up of solids on layers in the region of the rotor/stator.

In the afore-mentioned U.S. Pat. No. 5,546,791, Meeten sought a different way to mitigate the detrimental "end effects" discussed above. However, his remedy remained focused on the use of co-axial rotating cylinders, as employed in the outer rotor/inner stator arrangement (known as the "Couette geometry") and in the inner rotor/outer stator arrangement (known as the "Searle geometry"). Meeten's rheometer, while retaining a cup container and coaxial rotor/stator arrangement, introduced the use of a pump for providing a pulsatile, non-laminar flow intended for maintaining the particles in suspension while inducing a rheology effect for dispersing and maintaining relative dispersion of the particles and for remaining independent of the measuring system itself.

The present inventors believe that the use of a recirculating pump, as taught by Meeten, could introduce problems for evaluating relatively stiff and viscous mixes such as concrete and mortar. This is because such cementitious mixes, which begin to harden upon hydration, can potentially foul his hoses and pump equipment.

Moreover, it is possible that the effect of high viscous fluids in the hoses, such as cement slurries, pastes, or mortars, might tend to hinder the use of pulsing for dispersing the particles.

Accordingly, the present inventors believe that a novel device is needed for mixing and rheological measurement, one that is particularly capable of assessing the rheology of high viscosity fluids, and, especially, for particle suspensions such as cement slurries, pastes, and mortars.

SUMMARY OF THE INVENTION

In surmounting the disadvantages of the prior art, the present invention provides a device and method for achieving mixing and rheological evaluation of a wide variety of fluid sample types, including granular materials, particle suspensions (e.g., slurries and pastes), highly viscoelastic materials, and gas-solid mixtures.

The mixing and rheological measurement device of the present invention, otherwise referred to herein as a "rheomixer," is used in association with motor-driven rheology measurement machines that apply torque to the device and measure resistance of sample fluid in a container such as a cup. However, the novel and inventive features of the device minimize inaccuracies caused by "slippage at the wall" and "particle migration" effects previously described above.

One objective of the present invention is to provide a rotary rheological device that allows for integrated mixing and rheological evaluation of particle suspensions such as cementitious slurries, pastes, mortars, and concretes, whereby: (1) segregation of materials is minimized and fluid sample homogeneity is maintained; (2) three-dimensional mixing of particles and fluid is achieved; and (3) rheological properties are accurately evaluated using torque measurements, whereby detrimental effects caused by mixing (such as non-uniform particle dispersal) is minimized or avoided.

The present invention minimizes errors arising from transferring sample fluids between separate mixer and rheological testing devices. Errors due to exposure of sample fluid to ambient temperature and humidity, as well as due to loss or contamination of liquid sample during transferance, are greatly reduced.

An exemplary rheomixer device comprises: a rotatable shaft member having a generally elongate body; at least one blade attached to the shaft member and having a blade face angled to propel a liquid in a direction along the elongate shaft body when the shaft is rotated within the liquid; and at least one elongate shear-resistant member for resisting circular motion when the shaft member is rotated within the liquid, the at least one shear-resistant member being spaced at a fixed distance from, and being fixed in a rotational relationship with respect to, the at least one propeller blade; the shear-resistant member further being spaced apart from and attached in fixed spatial relation with respect to the rotatable shaft member. Preferably, the shear-resistant member is attached to a first end of the rotatable shaft and defines a circular path that preferably does not overlap or interfere with the circular path of the propeller blade when the device is rotated. The shear-resistant member(s) can be mounted in parallel or at an angle with respect to the rotatable shaft, while the propeller (mixing) blade(s) can be mounted perpendicularly or at an angle with respect to the shaft.

The invention also relates to methods wherein the above-described rheomixer is rotated within a sample liquid to mix the liquid, and rheology is assessed by measuring resistance of the liquid to rheomixer rotation.

In connection with cementitious liquid mixes, the rheomixer is used to mix water with hydratable cement (e.g., Portland cement, pozzolans such as granulated blast furnace slag, fly ash, gypsum, mixtures thereof) to provide a substantially uniform particle suspension that is hydratable and possesses a changing rheology whose changes can be measured over time. Thus, another exemplary method of the invention involves mixing dry components with water to provide a particle suspension (e.g., including "paste" or "slurry"), and thereafter measuring the rheology of the suspension, preferably over time, using the same rheomixer device, without having to transfer the sample liquid between separate mixer and rheology measurement devices.

The ability to mix and measure rheology with the same device is particularly advantageous for high-throughput mixing and testing of hydratable cementitious particle suspensions, and this can be done quickly in succession or in parallel on multiple samples. The quality of liquid samples can be adjusted during mixing and testing by addition of water, admixtures, solids, and other materials, without the back-and-forth transfers between separate mixer and rheology measurement devices.

Further exemplary rheomixers comprise a mix container for containing sample liquid. An optional lid or cover plate having an opening for the rotatable shaft is used to provide an adiabatic or semi-adiabatic mixing/rheology testing environment. In other exemplary embodiments, the mix container comprises and/or is surrounded by insulation material to insulate thermally the liquid contents from ambient air temperature fluctuations. The insulation may comprise a solid material, such as plastic, foam (e.g., polystyrene), glass, metal, or other material as desired. Further exemplary mix containers may also have cavities in the container walls for removing air, so as to create a vacuum; or water or other fluid may be pumped through the container walls, for example, to maintain the sample fluid at a desired temperature.

Preferred embodiments of the invention also comprise the use of at least one heat sensor (e.g., thermocouple, heat flow sensor) inside the mix container, within the container walls or floor, and/or on the outer surface of the container walls or floor. The heat sensor is operative to facilitate calorimetric measurements such as heat generated by the sample liquid over time. Preferably, the mix container comprises or is surrounded by insulation to insulate the liquid contents from ambient temperature and humidity fluctuations, thus helping the user to obtain uniformity of data from one mix-test to the next. Thus, the operations of mixing, rheological measurement, and calorimetric measurement may be accomplished in an integrated fashion.

Further exemplary methods of the invention involve mixing, rheological testing, and calorimetric testing to obtain data, from hydratable cementitious slurry samples, upon which set time and later strength characteristics (e.g., compressive strength) may be extrapolated.

In a further aspect of the invention, the mix container lid and body may be sealed so that the sample liquid can be pressurized. This enables the behavior of fluids such as used in subterranean applications (e.g., oil well, geothermal, drilling mud) to be studied under controllable pressure and temperature conditions.

Thus, a general purpose of the invention is to provide for mixing hydratable particle suspensions and measuring their rheological properties, including viscosity, yield value, and thixotropy, as a function of time and preferably within a closed system. The measurements can be used to characterize or predict the kinetics of hydration which in turn allow for the prediction of physical and mechanical properties in the resultant compositions after hydration. The rheomixer of the invention will, in particular, allow for accurate study of the effects of various additives and admixtures on the hydratable cementitious mixes.

As a broad concept, the present invention provides a device and method wherein a rheomixer comprises both mixing blades for mixing a liquid and shear-resistant members for measuring rheology of a liquid, a mix container having a heat sensor, and optionally a temperature control for maintaining a constant temperature in the container, a pressure control for maintaining a constant pressure in the container, or both temperature and pressure controls.

Further advantages and features of the invention are described hereinafter.

DETAILED DESCRIPTION OF EXEMPLARY EMBODIMENTS

The exemplary rheomixer of the present invention is designed to work with servo-controlled electric motors (otherwise referred to as "servo-engines") that are designed to rotate and to provide an electrical output signal that accurately corresponds to the amount of torque applied, such that, in combination with the inventive rheomixers of the present invention, fluid samples can be quickly mixed and their torque resistance on the rotated rheomixer device can be quickly and accurately measured. Such servo-engines are able to stop and start with high precision, due to the fact that their electric motors contain numerous electric coils that provide nearly-instantaneous torque. A servo-engine believed to be suitable for purposes of the present invention is available from Samey of Iceland under the tradename Control Technologies™, and other suitable servo-engines are elsewhere available.

Preferred methods of the invention for mixing involve the ability of servo-engines to alternate rotational directions, between clockwise and counter-clockwise rotation, and it is believed that this use of servo-controlled motors to agitate particle suspensions, such as cementitious compositions, may in itself be unique and novel. Unlike commercially available mixers for mortars and concretes, the, use of a servo-engine and rheometer may be employed for very low to very high agitation modes, thereby simulating the various mixing actions that occurs throughout the different commercial applications of cementitious suspensions.

The term "particle suspensions" as used herein means and refers generally to particles of matter that are suspended in a carrier fluid. Consequently, "cement" or "cementitious" particle syspensions include pastes, slurries, mortars, shotcrete, grouts (such as oil well cementing grouts), and concrete compositions having a hydratable cement binder. It is helpful to note that the terms "paste", "mortar" and "concrete" are terms of art. Pastes are mixtures composed of a hydratable cement binder (usually, but not exclusively, Portland cement, plaster, masonry cement, or mortar cement and may also include limestone, hydrated lime, fly ash, granulated blast furnace slag, pozzolans, silica fume, metakaolin, or other materials commonly included in such cements) and water; mortars are pastes additionally including fine aggregate (e.g., sand), and concretes are mortars that additionally including coarse aggregate (e.g., crushed gravel, crushed stone). Cementitious compositions can therefore be formed by mixing required amounts of certain materials, e.g., a hydratable cement, water, and optionally a fine aggregate (e.g., sand), coarse aggregate (e.g., crushed stone or gravel), or mixture of both fine and coarse aggregates. However, all of these hydratable cementitious compositions, which begin to hydrate upon mixing of the water and cementitious binder, are comprehended within the term "particle suspension."

Cementitious compositions may also include one or more cement additives or processing aids, or one or more concrete admixtures. A cement additive or processing aid is a chemical composition that is combined with cement clinker during intergrinding in the manufacture of cement from clinker. An admixture, on the other hand, is a material, other than cement, water, or aggregate, which is added generally to modify one or more properties of the resultant mortar, masonry mortar, concrete, or shotcrete. Accordingy, rheology devices of the invention may be used for mixing and measuring the rheology of a cement composition alone (e.g., cement slurry, paste, mortar, concrete, etc.), or a cement composition which additionally incorporates one or more additives or admixtures. In particular, the rheomixer devices of the invention are particularly suited for testing the effect of cement grinding (fineness), or, as further examples, the effect on the cement slurry or paste rheology of water reducers, superplasticizers, rheology modifiers, viscosity modifiers, air entrainers, and other admixtures.

Thus, in exemplary methods of the invention, additives and admixtures may be incorporated into the sample liquid being mixed and measured, such as by the use of a pump and capillary (tube fed) dosing system. The additives or admixtures can thus be mixed and their rheological effects tested without having to transfer the sample liquid between a separate mixer and separate rheology tester.

The rheology device may also be used for mixing and measuring rheology of other liquid samples such as latexes (e.g., paints), emulsions (e.g., wax, silicone, latex), colloidal suspensions, grease and lubrication compositions, asphaltic or bituminous compositions, adhesives, caulks, and other viscous fluids. A particularly preferred method involves measuring the rheology of coatings (such as primers, paints, mastics, adhesives, etc.) containing one or more types of particles (e.g., fillers such as sand, talc, clay, pigments, etc.). Paints, for example, are latexes that may optionally include sand, clay, or other fillers.

Figure 1:
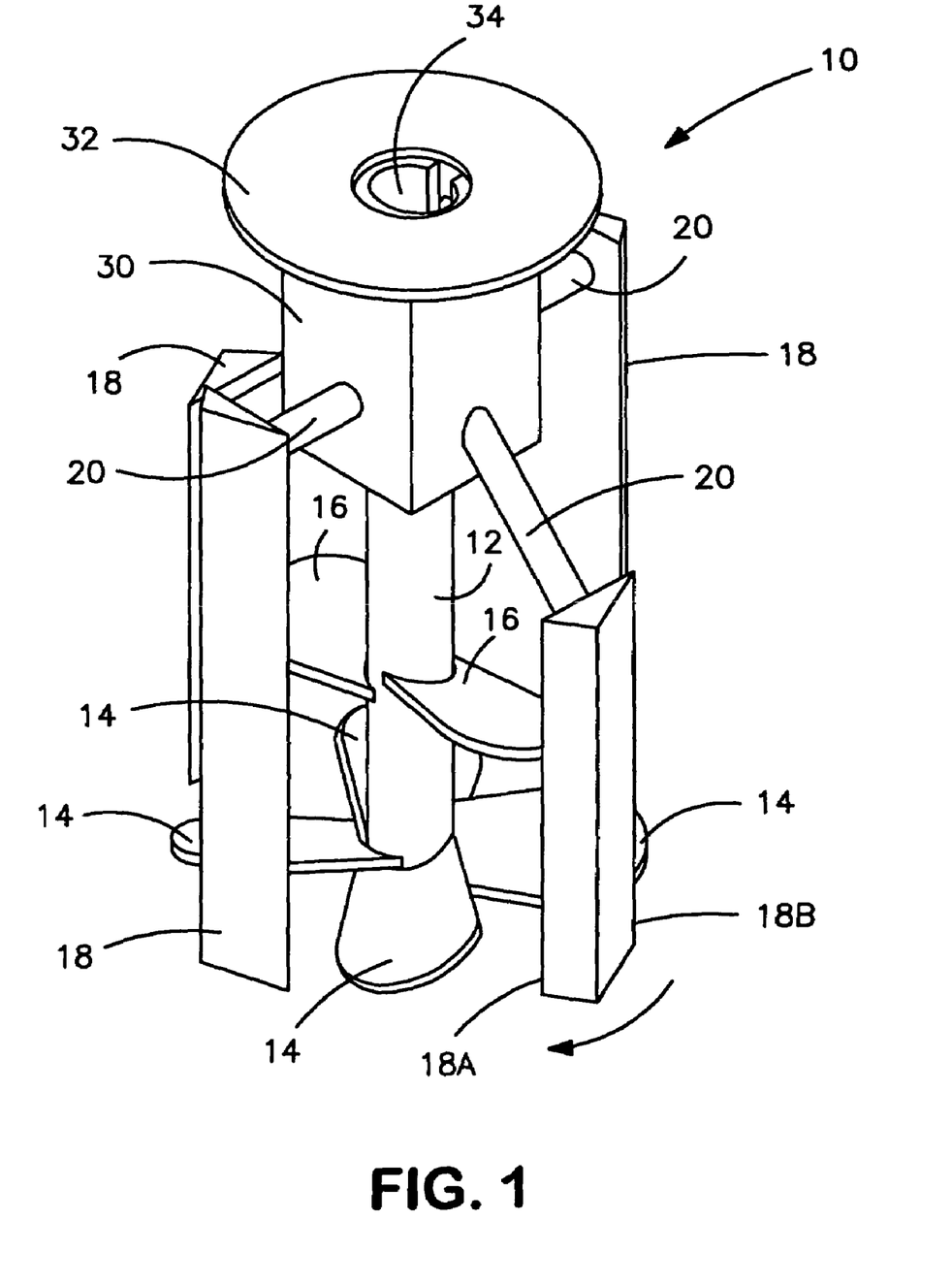
FIG. 1 is an illustration of an exemplary rheomixer device of the present invention.

As shown in FIG. 1, an exemplary device 10 for mixing and assessing the rheology of a sample liquid comprises a rotatable shaft member 12 having a generally elongate body, at least one (and more preferably more than one) propeller blade 14 attached to the shaft member 12 and having a blade face oriented to propel a viscous liquid sample (not shown) in a direction along the elongate shaft body 12 when the shaft 12 is rotated within the liquid sample; and at least one (and preferably more than one) elongate shear-resistant member 18 for resisting circular motion when the shaft member 12 is rotated within the liquid sample.

The at least one shear-resistant member 18 is spaced at a fixed distance from, and fixed in a rotational relationship with respect to, the at least one propeller blade 14. The at least one shear-resistant member 18 is also spaced apart from, and attached in fixed spatial relation with respect to, the rotatable shaft member 12. The shear-resistant member(s) 18 may be parallel or otherwise angled with respect to the rotatable shaft member 12, while the propeller blade(s) 14 may be perpendicular or otherwise angled with respect to the shaft member 12. Preferably, the rotational path of shear-resistant members should not overlap or coincide with the rotational path of propeller blades when the shaft is rotated about its axis.

In more preferred embodiments, the rotatable shaft member 12 has an elongate and preferably cylindrical body with first and second opposing ends, and a connector or collar member 30 located on the first (upper) end for connecting the device 10 to a mixing and torque-resistance-measuring servo-controlled motor or "servo-engine" (not illustrated) which is operative to rotate the shaft member 12 and provide a signal or indication of the resistance of the sample liquid to rotation.

The rotatable shaft member 12 should preferably be as thin and rigid as possible. If cylindrical in nature, the shaft 12 may be rotated about its circumferential axis, or even slightly off-axis in order to minimize agglomeration of particles or thickening of sample liquid on the shaft 12, although these effects are probably negligible. It is possible to alter the surface of the rotatable shaft member 12, such as by using elevated bumps, dimples, grooves, fish scale textures, or any number of surface disruptions, so as to decrease drag of liquid on the surface of the shaft, although any increase in accuracy due to the use of these if also probably negligible.

An optional circular mounting flange 32 is also shown attached to the collar member 30 at the upper end of the shaft 12 and surrounding a female receptacle 34 for coaxial attachment of the rheomixer 10 to a servo-controlled motor.

In preferred embodiments, a plurality of propeller blades 14 are located at or near the bottom of the rotatable shaft 12 as shown in FIG. 1. At least two, and more preferably four, blades 14 are preferably spaced at equal distances circumferentially around the shaft member 12, and have blade faces that are oriented preferably so as to push fluid in a direction upward along the elongate body of the shaft 12, when the shaft is rotated (in clock-wise fashion as suggested by the arrow). This bottom set of blades 14 are intended as the primary means for mixing the sample liquid.

Preferably, a plurality of propeller blades 16 is also located further upwards on the rotatable shaft 12 and spaced at equal distances circumferentially around the shaft 12. These blades 16 are situated such as to complement the mixing function of the primary blades 14, and are shown oriented with their faces to push sample fluid in a downward direction, when the shaft is rotated clock-wise, so as to disrupt the flow pattern of the liquid at the bottom of the mix container.

Where one or more sets of propeller blades 14 and 16 are used at different levels within the mix container, it is preferred that the primary mixing blades 16 located at the bottom of the container have a cumulative surface area (oriented in the upward pushing direction) that exceeds the cumulative surface area (oriented in the downward pushing direction) of the other (higher located) set or sets of blades (14). Especially for particle suspensions, in which particles tend to settle towards the bottom of the container, or migrate towards the walls, it is best that the primary bottom mixing blades 16 have the best chance of resisting the gravitation of particles downward. The other set or sets of blades 14 function in a manner that is secondary in that, by disrupting the flow patterns of the primary mixing blades 14, they ensure that the flow energy is dispersed throughout the entire volume of sample liquid.

Accordingly, as shown by the exemplary embodiment in FIG. 1, the face angles of the two blade sets 14/16 are preferably oppositely oriented. This will accomplish a "three dimensional" mixing of the fluid sample, whereby the agglomeration of particles around the shaft and settling of particles due to gravity are minimized. By mixing the fluid in "three dimensional" fashion, the exemplary rheomixer 10 constantly churns fluid within the container to maintain a relatively uniform dispersal of the particles.

Thus, a further exemplary device 10 of the present invention comprises a plurality of propeller blades 14 attached near or at the bottom of a rotatable shaft member 12; and a second plurality of propeller blades 16 attached to the shaft member 12 at a different position higher up on the shaft member 12, wherein the face angle of propeller blades of said first set 14 are oriented in a direction different from the face angle of propeller blades of the second set 16, and wherein the faces of the blades 14 located near or at the bottom of the rotatable shaft member are oriented so as to push fluid sample upwards when the rotatable shaft is rotated.

In some cases, it is preferable to have a small blade or tab located at the bottom surface of the rotatable shaft 12, to ensure that sample fluid residing between the bottom of the shaft and the floor of the mix container or cup is mixed and dispersed within the volume of the sample fluid, and agglomeration is avoided.

Exemplary mixing devices 10 of the present invention, as shown in FIG. 1, also comprise at least one shear-resistant member 18, and preferably at least two or more such shear-resistant members 18 spaced evenly around (or, in other words, equidistant circumferentially) the rotatable shaft member 12.

It is preferred that the shear-resistant members 18 be fixed spatially with respect to both the propeller blades 14/16 and shaft member 12. As shown in FIG. 1, the exemplary shear-resistant members 18 have a generally elongate body defined between opposite ends, and are preferably attached to the shaft member 12 (or the collar 30 member shown in FIG. 1) by brace members 20. Alternatively, the shear-resistant members 18 may be directly connected to the rotatable shaft 12 by braces 20. Preferably, the brace members 20 are situated higher than the uppermost propeller blades 16 such that the brace members 20 do not become immersed or substantially immersed in the fluid sample to be tested, and do not substantially introduce turbulence into the sample fluid being mixed and tested. The brace members 20 may assume generally any cross-sectional shape.

As further shown in FIG. 1, exemplary shear-resistant members 18 preferably have a tapered vertical leading edge 18A and tapered trailing vertical edge 18B operative to reduce or avoid cavitation (or agglomeration or other phenomena creating nonuniformity of viscosity) behind the shear-resistant member 18 when the device 10 is placed into a sample liquid and rotated. Preferably, the elongate shear-resistant member or members 18 is/are spaced apart from the shaft member 12 at a distance that exceeds the distance by which the propeller blades 14 and 16 extend from the shaft 12. Thus, it can be said that in such a preferred embodiment, the propeller blades 14 and 16 and shear-resistant members 18 have circular rotation paths that do not substantially coincide or intersect when the rheometer 10 is rotated.

Moreover, when a plurality of shear-resistant members 18 is employed (as shown in FIG. 1), it is preferred that they be attached to the rotatable shaft 12 in such a way that each shear-resistant member 18 does not travel precisely in the same orbital path as an immediately adjacent shear-resistant member. The shear-resistant member 18 shown in the right foreground (whose vertically extending edges are denoted "18A" and "18B") is shorter than the shear-resistant members located immediately adjacent, and is spaced at slightly greater distance from the rotatable shaft 12. In addition, the brace connector 20 for this shorter shear-resistant member is also angled differently from those shown to be connecting the two adjacent shear-resistant members 18 as well.

The purpose of having the different lengths and different spacings of the shear-resistance members 18 to minimize their cavitation effects (or agglomeration or particle migration effects) caused by their passage through the sample fluid medium. Ideally, at least two of the shear-resistance members should be spaced at different distances from the shaft 12, with the shorter member being preferably located a greater distance from the shaft. It is also preferred to position all shear-resistant members, whether they be long or short, such that their bottom portion travels close to the bottom of the container. The upper ends of the shear-resistant members are ideally used to connect them, using a connector 20, to the shaft 12 or (optional) collar member 30. It is also preferable to use different angles for positioning a connector 20, such that it does not have a rotational orbit coinciding with an immediately adjacent connector.

In further preferred embodiments, a portion of the propeller blades 14 and shear-resistant members 18 are positioned out-of-phase (and thus not aligned) with respect to each other, as shown in FIG. 1, to minimize further the possibility of inaccuracies caused by the propeller blades 14 on the sample fluid adjacent to circular pathways of the shear-resistant members 18 during rotation. Accordingly, in preferred devices 10 of the invention, the propeller blades 14 located bottommost on the shaft 12 comprise at least four blades 14 that are not radially aligned out with the shear-resistant members 18.

The rheometer device 10 can be fabricated from materials such as metals (e.g., steel), ceramics, plastics, resins, or other conventionally used materials.

Figure 2:
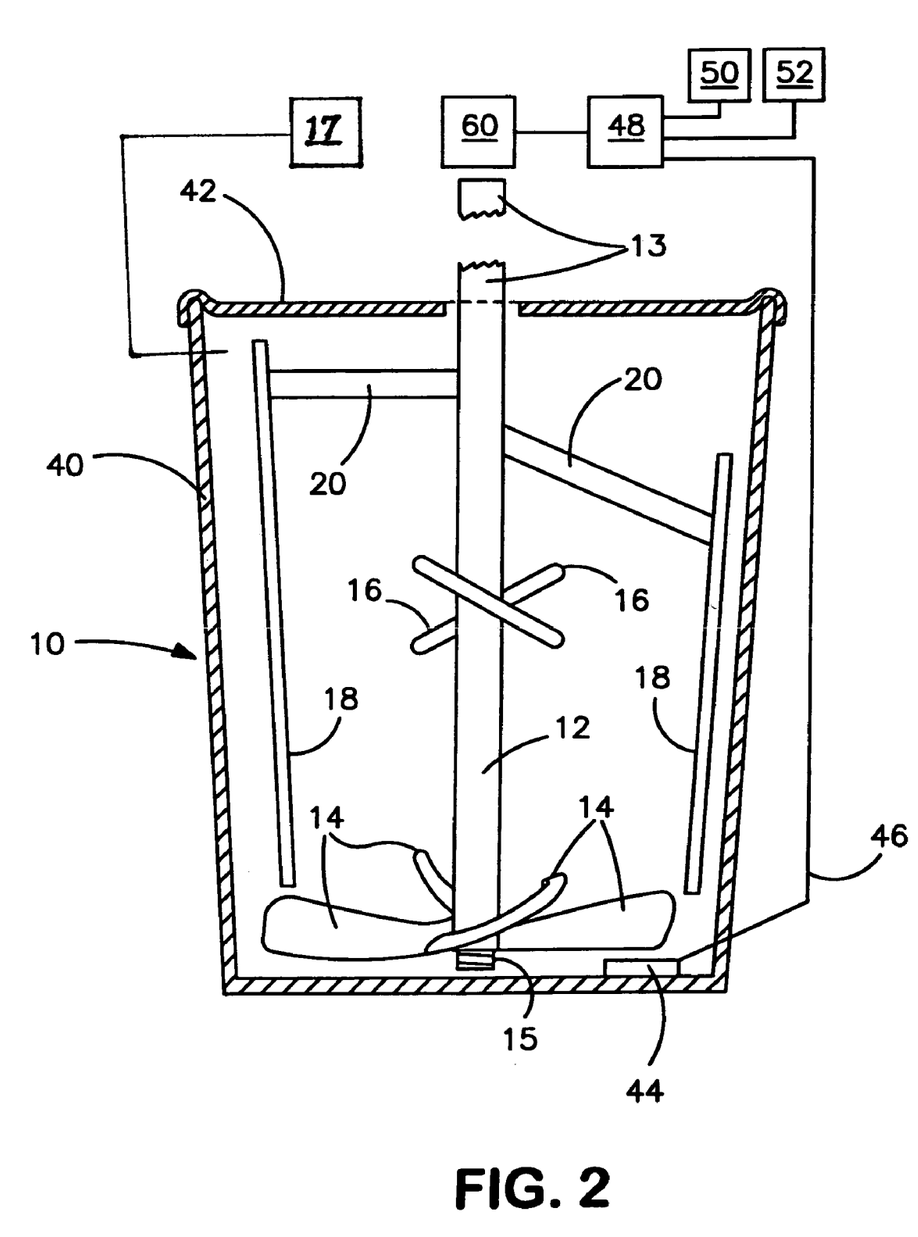
FIG. 2 is an illustration of another exemplary rheomixer device of the present invention.

As shown in FIG. 2, another exemplary rheomixer 10 of the invention comprises the mixing/testing device 10 and mixing container 40 with optional lid 42. This will provide partially adiabatic testing of rheology and heat of hydration and other chemical reactions. The lid 42 contains an opening for the rotatable shaft 12. For the sake of simplicity, two sets of mixing propeller blades 14 and 16 are shown spaced apart vertically on and connected to the shaft 12, as is an optional wiping element 15, which can have a thin tab shape or other shape, for agitating liquid between the bottom surface of the shaft 12 and the floor of the container 40, to prevent agglomeration and facilitate uniform dispersion. Two shear-resistant members 18 are also shown having different lengths, preferably the shorter member is located further away from the shaft 12, and both need not necessarily be disposed parallel to the shaft but can be angled to conform with the slope of the container walls, such as plastic coffee cups, to dead spots.

Shear-resistant members 18, incidently, can be connected to the rotatable shaft using a connector shaped as a bar, as shown, or using any other shapes (such as a circular disk or flat member.

As further illustrated in FIG. 2, an exemplary rheomixer 10 of the present invention includes, a mixing container 40 and cover 42, which may be a plastic coffee cup 40 and plastic lid 42, to provide for adiabatic or partial-adiabatic testing of the sample liquids. A heat sensor 44 is located within the mix container 40 for measuring heat output of the liquid sample, and may otherwise be embedded with the walls or floor of the container body. Electric wires from the heat sensor can be run through the container wall (and sealed with tape) or lead out between the container rim and cover. The cover 42 has an opening for passage of the upper shaft 13 which is connected to a servo-control motor 60. The container 40 and cover 42 may be made of various materials, such as insulative polystyrene foam, plastic, metal, or other material. The use of plastic, for example, will make it easy to provide holes for various uses, such as for passing heat sensor 44 wires into the containers. Holes in the cover may also be used for introducing water, admixtures, solids, or other materials into the liquid sample. The ability to make the container 40 and cover 42 using inexpensive materials is advantageous for mixing and testing of cementitious samples which can be discarded after the mix hardens without economic hardship.

As mentioned above, the rheomixer 10/40 shown in FIG. 2 can further comprise the use of a heat sensor 44 (e.g., thermocouple, heat flow sensor, infrared detector). The wire leads 46 from the heat sensor 44 (can be taped against the inner wall of the mixing container 40, and can be accessed by running them over the top edge of the container 40 and between the cover 42, or, by running them through the wall as illustrated (using tape which is not illustrated). If the mixing container is a foamed polystyrene cup, the heat sensor 44 can be physically embedded in the soft inner wall so that it presents minimal impedance to flow of the sample liquids being mixed and measured. The wire leads 46 are used for connecting the thermocouple to a computer processing unit 48 which can also be used for electrically connecting the servo-motor 60 and controlling the mixing and rheological measurements of the sample being mixed. A data logger 50 and memory 52 for containing information such as reference temperature profiles are also electronically connected to the computer processing unit 48.

Thus, the rheomixer device, as illustrated in FIG. 2, can be used as a self-contained system for evaluating and predicting basic properties of a hydrating cementitious mixture sample, and is well-suited for automation and high throughput testing. For example, the rheomixer 10 can be used to mix the sample fluid, even when starting from an initial mixture of water and dry powder materials, and can measure rheology over a period of time and as a function of time, eliminating the need to transfer the mixture from a mixer or blender to a separate rheology measurement device. At the same time, it protects the mix sample from evaporation and thermal fluctuations due to the outside environment, and ensures accurate rheology measurements by periodic mixing in an automated fashion.

Then the heat evolution of the mix sample can be measured as a function of time, typically 24 hours to several days. The heat evolution can be measured partially adiabatically and/or isothermally using a heat flowsensors 44 that is preferably installed within the mix container 40, and optionally using a temperature control device or system (e.g., heating coils, liquid bath) around the mix container or built into the mix container to maintain a controlled temperature. Although the sample can be transferred from the mix container 40 into an isothermal calorimeter (which is kept at a desired, contant temperature), the sample may also be measured semi-adiabatically using the heat sensor 44 installed within the mix container 40. As the rheomixer 10 can be made relatively inexpensively, it can be removed, washed, and reused, or it may be simply left in the hydrating mix along with the heat sensor and (preferably insulated) mix container at the end of testing.

The computer processing unit 48 and data logger 50 may employ software that employs known relationships between rheological and calorimetric data to convert output signals from the servo-motor 60 into flow and workability performance characteristics of cementitious mixture samples before setting/curing of the mixture. This information is useful for optimizing mixture proportions as well as type and dosage amounts of chemical admixtures (e.g., water reducers, plasticizers, fluidiers, set accelerators, set retarders, etc.) to reach a particular performance target. The software may also employ known relationships to convert heat evolution data to provide an indication of the degree to which the cementitous binder is hydrated. Thus, for example, a computer monitor or printer may be connected to the computer processing unit 48 or data logger 50 to provide visual indication, in terms of a percentage number, or as a bar graph or other graphic or pictorial means, of the degree of hydration of the cementitious binder. The degree of hydration can further be used to compute initial and final setting of the cementitious binder, as well as to provide an indication, such as in terms of a percentage number or as a bar graph or other graphic or pictorial means, of strength development in the sample mixture.

Accordingly, an exemplary method of the invention comprises providing the aforementioned rheomixer 10 in a mixing container 40, such as in a foamed polystyrene cup, with water, a hydratable cementitious binder, optionally with aggregates and/or admixture(s), and mixing these components together to provide a slurry. The rheology of the mixture is assessed using the rheomixer 10 immediately upon completion of this initial mixing event, and subsequently thereafter at successive time periods. The rheological property of the sample mix may then be recorded as a function of time, and thus the degree of hydration may be plotted or displayed graphically as a function of time (e.g., first 60 minutes, 12 hours, 24 hours etc.). Simultaneously with these measurements, or apart from them, the heat evolution of the mixed sample can also be measured as a function of time (e.g., one hour, 12 hours, 48 hours, 28 days, etc.). The rheological and calorimetric measurements can be accomplished within the same mix container, without having to transfer the sample from a separate mixer to a separate rheological measurement device; or from a mixer or rheological measurement device to a separate calorimetric measurement device.

Further exemplary methods of the invention comprise obtaining rheological and calorimetric (e.g., heat evolution)

data from a hydratable cementitious composition over a period of time, using the device illustrated in FIG. 2, comparing the obtained data with pre-established relationships or correlations between rheological data and/or calorimetric data and properties of the cured cementitious composition (such as strength, set time, etc.), and extrapolating one or more later properties of the cured cementitious composition based on the rheological data and calorimetric data obtained. In further exemplary methods, the relationship between the data over time can be plotted as a function of hydration and/or strength over time, and graphically displayed by the computer processing unit on graph paper or a monitor screen connected to the computer processing unit.

The combination of a (1) mixer/rheology measurement device and a (2) mixing container containing a heat sensor has not previously been taught or suggested in the prior art. The use of a mixer/rheology measurement device is not limited to the one described and illustrated herein. It is believed that other devices which operate to mix a hydratable cementitious slurry from its separate components can be used to achieve this aspect of the invention. Accordingly, a further exemplary device and method of the invention involves this combination of (1) mixer/rheology measurement device and a (2) mixing container containing a thermocouple, preferably with the container providing an adiabatic or partially adiabatic environment (such as the case of using a plastic coffee cup and cover or lid).

In still further exemplary embodiments, the sample liquid may be pressurized so that the contained liquid sample may be tested under pressure. As mentioned in the summary, this would be beneficial for testing sample liquids, such as well drilling cements, which are customarily subjected to high pressure. Thus, exemplary mix containers 40 and covers 42 of the present invention may be constructed so as to become, sealed together so that air, oxygen, carbon dioxide, or inert gases can be pumped into the mix container in order to elevate pressure upon the sample liquid. One may optionally employ a seal around the rotatable shaft 12 of the rheometer 10 and calibrate the servo-motor device 60 to account for frictional forces introduced by the seal. One may optionally employ a pressure control 17 for maintaining a constant pressure in the container.

In still further exemplary embodiments, the sample liquid may be pressurized so that the contained liquid sample may be tested under pressure. As mentioned in the summary, this would be beneficial for testing sample liquids, such as well drilling cements, which are customarily subjected to high pressure. Thus, exemplary mix containers 40 and covers 42 of the present invention may be placed within, or constructed so as to become, sealed together so that air, oxygen, carbon dioxide, or inert gases can be pumped into the mix container in order to elevate pressure upon the sample liquid. One may optionally employ a seal around the rotatable shaft 12 of the rheometer 10 and calibrate the servo-motor device 60 to account for frictional forces introduced by the seal.

Accordingly, the present invention provides devices and methods for mixing, rheological testing, and calorimetric testing, which can be done under controllable temperature and pressure conditions without having to transfer fluid between separate mixing, rheological, and calorimetric devices. Such integrated operations may be automated on a high through put basis using computer processing units.

The invention is not intended to be limited by the foregoing examples and preferred embodiments which are provided for illustrative purposes only.

It is claimed:

1. Method for assessing a sample liquid, comprising: mixing within a container a sample liquid and assessing the rheology of said sample liquid, said mixing and assessing comprising the use of a device having a rotatable shaft member having a generally elongate body, at least one propeller blade attached to said shaft member and having a blade face oriented to propel a liquid in a direction along said elongate shaft body when said shaft is rotated within a liquid, and at least one elongate shear-resistant member for resisting circular motion when said shaft member is rotated within the liquid, said at least one shear-resistant member being spaced at a fixed distance from, and being fixed in a fixed rotational relationship with respect to, said at least one propeller such that said at least one shear-resistant member is rotated when said at least one propeller blade is rotated, and said at least one shear-resistant member being spaced apart from and attached to said rotatable shaft member; and measuring the heat or temperature of said sample liquid over time by employing a sensor in said container.

2. The method of claim 1 wherein said sample liquid is selected from the group consisting of latexes, emulsions, colloidal suspensions, grease, lubricants, asphaltic compositions, adhesives, caulks, and particulate suspensions.

3. The method of claim 1 wherein said container contains a hydratable cementitious particle suspension.

4. The method of claim 3 wherein said container further comprises a lid or cover plate having an opening corresponding to said rotatable shaft member whereby an adiabatic or semi-adiabatic mixing and rheology testing environment is provided within said container.

5. The method of claim 1 wherein said sensor is a thermocouple, heat flow sensor, or infrared detector.

6. The method of claim 1 wherein said sensor is electronically connected to a data logger for collecting heat measurements over time.

7. The method of claim 6 wherein said sample liquid is a hydratable cementitious particle suspension, said method further comprising computing data relative to degree of hydration of said hydratable cementitious particle suspension.

8. The method of claim 6 wherein the container contains a hydratable cementitious particle suspension and at least one chemical admixture, said method comprising computing data relative to degree of hydration of said hydratable cementitious particle suspension and said admixture.

9. The method of claim 1 further comprising obtaining rheological and calorimetric data from a sample liquid within the container over a period of time; comparing the obtained data with pre-established relationships or correlations between rheological data, calorimetric data, or both of said rheological and calorimetric data; and extrapolating at least one later property of the sample liquid when cured, said property comprising strength or set time.

10. The method of claim 9 wherein said container comprises a hydratable cementitious particle suspension.

11. The method of claim 1 further comprising measuring rheology and heat or temperature over time without transferring sample liquid from said container.

12. The method of claim 11 wherein said measuring of rheology and heat or temperature over time is automated using a computer processing unit.

13. The method of claim 1 further comprising maintaining a constant temperature in said container.

14. The method of claim 1 further comprising maintaining a constant pressure in said container.

15. The method of claim 1 further comprising maintaining constant temperature and constant pressure in said container.

16. The method of claim 1 wherein said rotatable shaft member is attached to a servo-engine operative to rotate and provide an electrical output signal corresponding to the amount of torque applied.

17. The method of claim 16 further collecting heat or temperature information using said sensor; storing said information in a data logger which is electronically connected to said sensor; obtaining electrical output signals from said servo-engine and converting said electrical output signals into flow performance characteristics of said sample liquid.

18. The method of claim 1 wherein container contains a hydratable cementitious particle suspension, said method comprising obtaining heat evolution data using said sensor over time and converting said heat evolution data to obtain an indication of the degree to which said hydratable cementitious particle suspension is hydrated over time.

19. The method of claim 18 comprising mixing and assessing the rheology and heat or temperature of a hydratable cementitious particle suspension containing at least one chemical admixture selected from the group consisting of a water reducer, a plasticizer, a set accelerator, and a set retarder.

20. The method of claim 18 further comprising predicting an initial setting and final setting of said hydratable cementitious particle suspension.

21. The method of claim 20 wherein said initial and final settings of said hydratable cementitious particle suspension are indicated in terms of a percentage number, graphically, or pictorially.

22. Method for testing of a hydratable cementitious particle suspension, comprising:

mixing within a container a hydratable cementitious particle suspension, said suspension optionally containing at least one chemical admixture selected from the group consisting of a water reducer, a plasticizer, a set accelerator, and a set retarder;

assessing the rheology of said hydratable cementitious particle suspension;

said mixing and assessing comprising the use of a device having a rotatable shaft member having a generally elongate body, at least one propeller blade attached to said shaft member and having a blade face oriented to propel said hydratable cementitious particle suspension in a direction along said elongate shaft body when said shaft is rotated within a liquid, and at least one elongate shear-resistant member for resisting circular motion when said shaft member is rotated within said hydratable cementitious particle suspension, said at least one shear-resistant member being spaced at a fixed distance from, and being fixed in a fixed rotational relationship with respect to, said at least one propeller blade such that said at least one shear-resistant member is rotated when said at least one propeller blade is rotated, and said at least one shear-resistant member being spaced apart from and attached to said rotatable shaft member; and measuring the heat or temperature of said hydratable cementitious particle suspension over time by employing a sensor in said container.

23. Method for assessing a sample liquid, comprising:

mixing within a container a sample liquid and assessing the rheology of said sample liquid, said mixing and assessing comprising the use of a device having a rotatable shaft member having a generally elongate body, at least two sets of propeller blades attached to said shaft member at different positions on said shaft member, the blades having faces oriented to propel a liquid in a direction along said elongate shaft body when said shaft is rotated within a liquid, and at least one elongate shear-resistant member for resisting circular motion when said shaft member is rotated within the liquid, said at least one shear-resistant member being spaced at a fixed distance from, and being fixed in a fixed rotational relationship with respect to, said propeller blades such that said at least one shear-resistant member is rotated when said at least one propeller blade is rotated, and said at least one shear-resistant member being spaced apart from and attached to said rotatable shaft member;

said at least one shear-resistant member having a tapered vertical leading edge and a tapered trailing vertical edge operative to reduce cavitation in said sample liquid when said device is placed into said sample liquid within said container and rotated; and measuring the heat or temperature of said sample liquid over time by employing a sensor in said container.

\* \* \* \* \*